United States Patent [19]

Blair et al.

[11] Patent Number: 5,164,604
[45] Date of Patent: Nov. 17, 1992

[54] MULTIPORT PARTICLE DETECTION APPARATUS UTILIZING A PLENUM HAVING A PLURALITY OF SPATICALLY SEPARATE CHANNELS IN FLUID COMBINATION

[75] Inventors: Harvey V. Blair; John McLin; Joseph F. Halik, all of Tucson; William J. Coates, Oro Valley, all of Ariz.

[73] Assignee: Allied-Signal Inc., Morris Township, Morris County, N.J.

[21] Appl. No.: 694,188

[22] Filed: May 1, 1991

[51] Int. Cl.$^5$ .............................................. G01N 15/06
[52] U.S. Cl. .................................. 250/574; 250/575; 356/343
[58] Field of Search ................. 250/574, 575; 356/438, 356/439, 343; 340/630

[56] References Cited

U.S. PATENT DOCUMENTS

| | | | |
|---|---|---|---|
| 4,017,193 | 4/1977 | Loiterman | 356/206 |
| 4,556,873 | 12/1985 | Yamada et al. | 340/630 |
| 4,642,471 | 2/1987 | Guttinger et al. | 250/574 |
| 4,647,785 | 3/1987 | Morita | 250/574 |
| 4,678,921 | 7/1987 | Nakamura et al. | 250/573 |
| 4,749,871 | 6/1988 | Galvin et al. | 250/574 |
| 4,769,550 | 9/1988 | Dolnick | 250/574 |
| 5,011,286 | 4/1991 | Petralli | 356/343 |

OTHER PUBLICATIONS

Article from Dec. 1972 Technical News Bulletin entitled "New Apparatus Determines Particle Size Distribution in Real Time".
Technical Paper entitled "Laser Smoke Detection" by Dr. David K. Duston Espey Manufacturing & Electronics Corp., Saratoga Springs, N.Y. no date.
Article from Nov./Dec. 1980 Optical Engineering entitled "Laser-Based Single Particle Counters for in Situ Particulate Diagnostics" by F. Dan Hirleman.

*Primary Examiner*—David C. Nelms
*Assistant Examiner*—T. Davenport
*Attorney, Agent, or Firm*—Joseph R. Black; Hugh P. Gortler; Robert A. Walsh

[57] ABSTRACT

Detection apparatus employs a plurality of conduits, a plurality of photosensors, and a laser in a multi-port forward-scattering geometry to detect particles for each of a plurality of spatial sections ($S_1$, ... $S_n$) of an enclosure. The photosensors are provided in two sets arranged at two different scattering angles to discriminate smoke from other particulate matter in sample flows which flow along the conduits and intersect the laser beam. The sample flows are discharged into a plenum and removed from the plenum via a single manifold. The laser can be backed up by an auxiliary laser.

20 Claims, 5 Drawing Sheets

MULTIPORT PARTICLE DETECTION APPARATUS UTILIZING A PLENUM HAVING A PLURALITY OF SPATIALLY SEPARATE CHANNELS IN FLUID COMBINATION

TECHNICAL FIELD

The invention relates generally to particle detection. More specifically, the invention relates to a multiport particle detector adapted to detect smoke in each of a plurality of spatial sections of an enclosure.

BACKGROUND OF THE INVENTION

In environments such as buildings, large ocean-going vessels, and flight craft it is highly desirable to detect smoke at the earliest possible moment, to do so for a large number of spatial sections of the environment in which smoke is to be detected, and to do so without communicating spurious indications of the presence of smoke. The ability to meet these needs is complicated by considerations including cost, technology, and human factors. For example, if a smoke detection system designed for a large building requires a source/detector combination for each of a large number of spatial sections, then the initial cost and projected maintenance costs for the system may render it cost prohibitive, thus forcing resort to cheaper but less effective fire protection schemes. As a further example, the detection of smoke in an environment containing normal airborne particulate matter such as common dust presents the problem of distinguishing between the normal particulates and those accompanying smoke. If the smoke detection system does not consistently make that distinction, then it will occasionally communicate spurious indications of the presence of smoke. Avoiding undesirable electromechanical and/or human-behavioral responses then requires that the system incorporate some form of verification. This necessarily decreases the efficiency of the system and may significantly increase its cost.

SUMMARY OF THE INVENTION

The apparatus comprises means for forming a plurality of spatially separate channels, a manifold to which the forming means is secured so that the channels are in fluid communication with a manifold plenum, a plurality of photosensors, each operatively associated with its own one of the channels, and a laser selected to produce a beam of electromagnetic radiation which interacts with particles by scattering, the laser being positioned relative to the channels such that the particles can intersect the beam in flowing from the channels to the plenum, and each photosensor being positioned relative to its operatively associated channel such that radiation scattered from dust which intersects the beam can impinge the photosensor.

Smoke detection apparatus employs a forward-scattering geometry and further comprises a second plurality of photosensors, each operatively associated with its own one of the channels. With that arrangement, first and second photosensors are operatively associated with each channel and are positioned at two different scattering angles in relation to the beam. The first is positioned at a reference angle which renders the photosensor substantially unresponsive to optical differences between smoke and other particles. The second is positioned at a measurement angle which renders the photosensor significantly responsive to optical differences between the forementioned particles. Smoke detection is based on a ratio of signals derived from the two photosensors.

DETAILED DESCRIPTION OF THE PREFERRED EMBODIMENTS

Figures 1, 4, 4A:
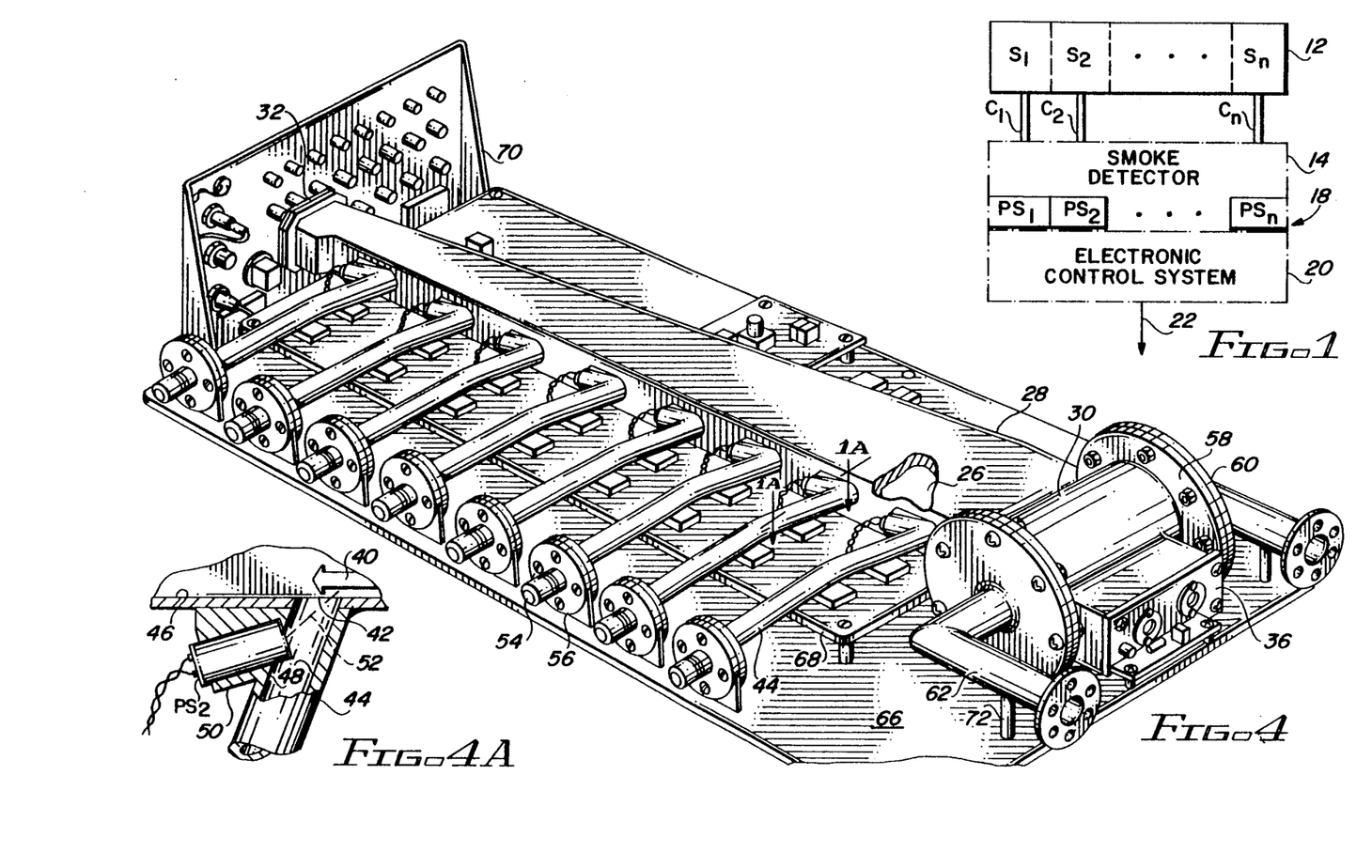
FIG. 1 is a highly schematic illustration of the invention in use.
FIG. 4 is a perspective view of a further embodiment of the invention.
FIG. 4A is a fragmentary cross-sectional view taken as indicated in FIG. 4.

FIG. 1 of the drawings schematically depicts an enclosure 12 containing a plurality of spatial sections $S_1$, $S_2, \ldots S_n$. The enclosure 12 may be a building, a cargo bay of an aircraft, or an undersea vessel, for example. Projecting from the enclosure sections $S_1, S_2, \ldots S_n$ are a corresponding plurality of conduits $C_1, C_2, \ldots C_n$. The conduits $C_1, C_2, \ldots C_n$ are connected to and in fluid communication with a corresponding plurality of conduits (not illustrated in FIG. 1) which form structural elements of a detection apparatus 14 (hereinafter "detector"). The detector 14 includes a plurality of photosensors $PS_1, PS_2, \ldots PS_n$ one for each of the unillustrated conduits, and may include further photosensors as more particularly described hereinafter. The detector 14 is part of a detection system 18 which also includes an electronic control system 20. The control system 20 includes conventional signal processing and system processing hardware interfaced with the photosensors $PS_1, PS_2, \ldots PS_n$ as subsequently described to produce one or more outputs 22 indicating status and/or an alarm condition. The detection system 18 may also include one or more blower motors 24 for forcing air flow from the spatial sections $S_1, S_2, \ldots S_n$ through the detector 14. Alternatively, the air flow may be effected by functionally similar apparatus contained in the enclosure 12.

Reference is made to FIGS. 4 and 4A which illustrate a constructed and tested embodiment of the detector 14 employing a single photosensor per channel in a forward-scattering geometry. A plenum 26 is formed by welding together a first manifold 28 of rectangular cross-section and a second manifold 30 of circular cross-section. The second manifold 30 has opposing openings formed through its wall to accommodate fluid and optical communication with the first manifold 28 and a laser source module 36, respectively, both being connected in sealing relation to the second manifold 30. The first section 28 converges as shown to a remote end which is welded to an endplate 26. The endplate 26 is adapted by suitable means for installation of an obscuration-monitoring photosensor 34 (FIG. 10) which is positioned to receive electromagnetic radiation (EMR) transmitted along the plenum 26 from the laser source module 36. The module 36 contains a conventional laser, preferably in the form of a laser diode 38 of the type equipped with an internal photosensor which is used to monitor the output of a laser chip (e.g. NDL-series laser diodes available from NEC Electronics Corporation). The laser 38 is positioned to transmit its beam 40 directly toward the obscuration - monitoring photosensor 34 and diametrically across the aligned ports 42 formed by a plurality of conduits 44 brazed to the first manifold 28. The first manifold 28 has a corresponding plurality of holes formed through the indicated wall 46 to accommodate fluid and optical communication. The conduits 44 are provided in the form of generally tubular members forming a plurality of spatially separate channels 48. Small branching tubes (as at 50) are provided for installation of photosensors $PS_2$, and the latter are positioned relative to the beam 40 such that radiation scattered therefrom can centrally impinge the photosensor by a direct linear path (indicated by line 52).

Preferably, the linear path 52 bears relative to the beam 40 at the lowest forward-scattering angle which can be attained within the geometrical limitations of the selected structure. The invention can be used to advantage over a wide range of scattering angles. However, results are significantly degraded at higher angles and become substantially impracticable at about sixty degrees.

Figure 2:
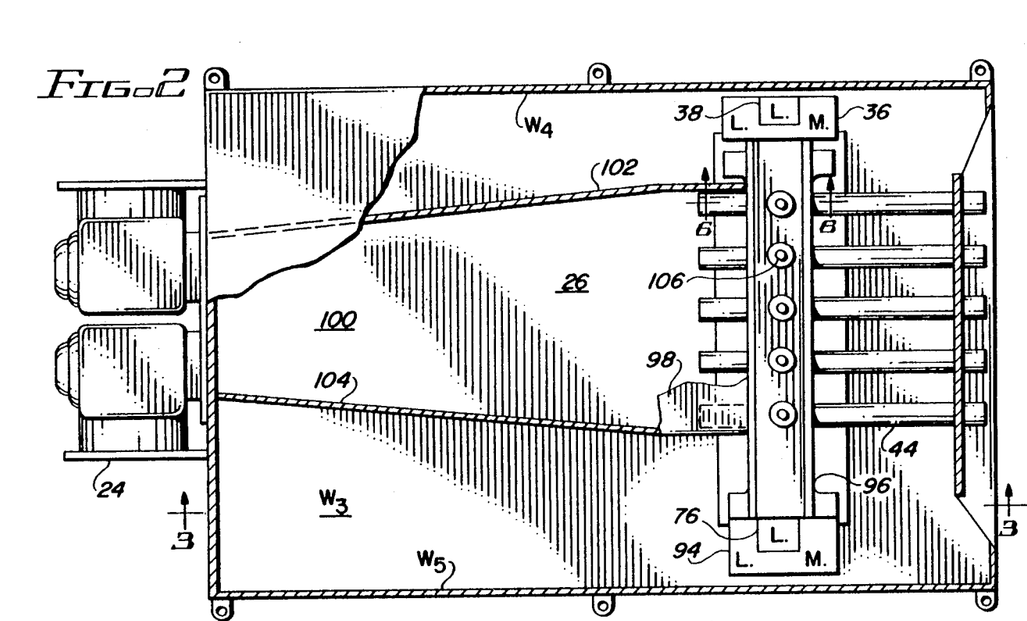
FIG. 2 is a generally elevational, partially cross-sectional, and slightly schematic view of an embodiment of the invention, taken along line 2—2 of FIG. 3.

The conduits 44 extend to distal ends 54 thereof, and are provided with annular flange adaptors 56 for connecting to the conduits $C_1, C_2, \ldots C_n$ indicated in FIG. 1. The second manifold 30 is also provided with annular flanges 58 which are connected to mating flanges 60 welded to vent pipes 62. The latter are similarly adapted for securement to blower motors 24 (FIG. 2).

The smoke detector 14 is shown mounted on a baseplate 66, as are all circuit boards 68 required for the electronic control system 20 (FIG. 10), a current driver for the laser diode 38, and monitoring circuitry for the internal photosensor (not shown) in the laser diode. The detector 14 is secured at one end to a connector panel 70 which is fixed to the baseplate 66, and at the opposite end to the vent pipes 62 which are fixed to support rods 72 extending upwardly from the baseplate.

FIGS. 2, 3, 5, and 6 depict the apparatus adapted for use as a smoke detector 14. In terms of structure, this differs from the previously described embodiment in three important respects. First, there are two opposing lasers, a main laser 38 and an auxiliary laser 76, only one being operational at a particular time. Second, the laser beam 40 is transmitted directly through all of the conduits 44. Third, two photosensors detect different scattering angles 82, 84 for each conduit 44.

Figure 11:
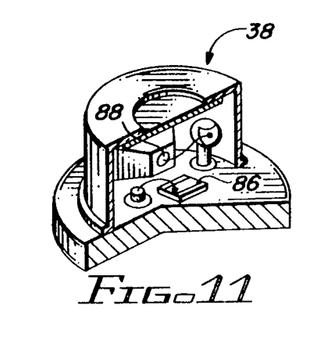
FIG. 11 is a perspective and partially cross-sectional illustration of a conventional laser diode.

The opposing pair of lasers 38, 76 provides redundancy as a safety feature in the event of failure of the main laser 38. The invention can be practiced in the reverse-scattering geometry to which conversion would be made in that event. However, as indicated above, a forward-scattering geometry is preferable. The use of laser diodes such as that indicated in FIG. 11 provides the capability of using the internal reference photodiode 86 of one laser to measure total obscuration of the beam emitted by the other. To that end, the lasers 38, 76 are positioned so that their emitted beams are substantially aligned. Any obscuration of the beam attributable to the laser chip 88 (FIG. 11) of the opposing laser diode is constant, and does not inhibit the ability to determine obscuration of the beam. An important added advantage of this arrangement is that any mechanical shifting of the main laser 38 can be detected by the internal photodiode of the auxiliary laser 76. Such shifting would result in reorientation of the beam 40, and the outputs of photosensors $PS_1, PS_2, \ldots PS_n$ could then significantly change for a given level of scattering. Consequently, the ability of the control system 20 to detect an alarm condition in accord with predetermined specifications could be impaired. In that event, the system 20 would switch to use of the auxiliary laser 76.

Transmission of the beam 40 directly through the conduits 44 facilitates the use of plural scattering angles by eliminating mechanical limitations inherent in the structure illustrated in FIG. 1. The use of plural scattering angles provides the ability to distinguish smoke particles from other particles in the air stream, thereby avoiding false alarms caused by the latter class of particles.

Figure 3:
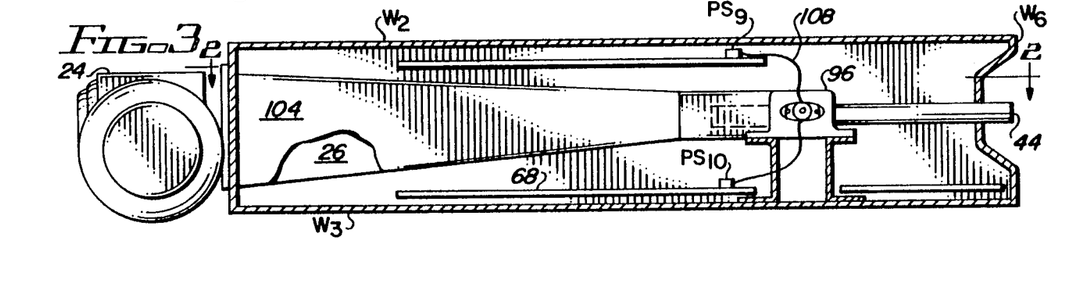
FIG. 3 is a partially cross-sectional and partially elevational view taken along line 3—3 of FIG. 2, and adding schematic representation of electronic elements.

The smoke detector 14 is formed within an encasement having six walls $W_1 \ldots W_6$. The forward wall $W_1$ has an opening formed therethrough and is otherwise adapted for installation of blower motors 24 such that the latter are rigidly secured to the wall $W_1$ and in fluid communication with the plenum 26. Circuit boards (as at 68) are secured by conventional means (not shown) to the top and bottom walls $W_2$, $W_3$. Two elongate C-brackets 90, 92 are rigidly secured to the bottom wall $W_2$, $W_3$. The C-brackets support main and auxiliary laser modules 36, 94, and an interconnecting shroud 96. The shroud 96 isolates the beam 40 from the surrounding environment, rigidly supports the conduits 44 which extend through the shroud to the plenum 26, and rigidly supports top and bottom walls 98, 100 of the manifold. The latter is formed by four walls 98, 100, 102, 104 as indicated. The shroud 96 has holes 106 formed through its top face to accommodate receipt of a first set of fiber optics 108. The conduits 44 extend through and are rigidly secured to the rear wall $W_6$ of the encasement.

Each of the fiber optics 108 extends from a photosensor $PS_1$ or $PS_3$ or $PS_5$ or $PS_7$ or $PS_9$ to an operatively associated conduit 44 and is fitted in the latter at a location corresponding to a scattering angle 82 of ninety degrees in relation to the beam 40. At angles in the range of about eighty-five to about ninety-five degrees, scattered radiation intensity if substantially the same for dust and smoke particles at any particular obscuration level. Each fiber optic 112 in a second set thereof extends from a photosensor $PS_2$ or $PS_4$ or $PS_6$ or $PS_8$ or $PS_{10}$ to an operatiavely associated conduit 44 and is fitted in the latter at a location corresponding to a forward-scattering angle 84 of thirty degrees in relation to the beam 40 of the main laser 38. The lower the scattering angle 84, the higher is the difference between scattered radiation intensities for dust and smoke at any particular obscuration level.

Figures 5, 7, 10:
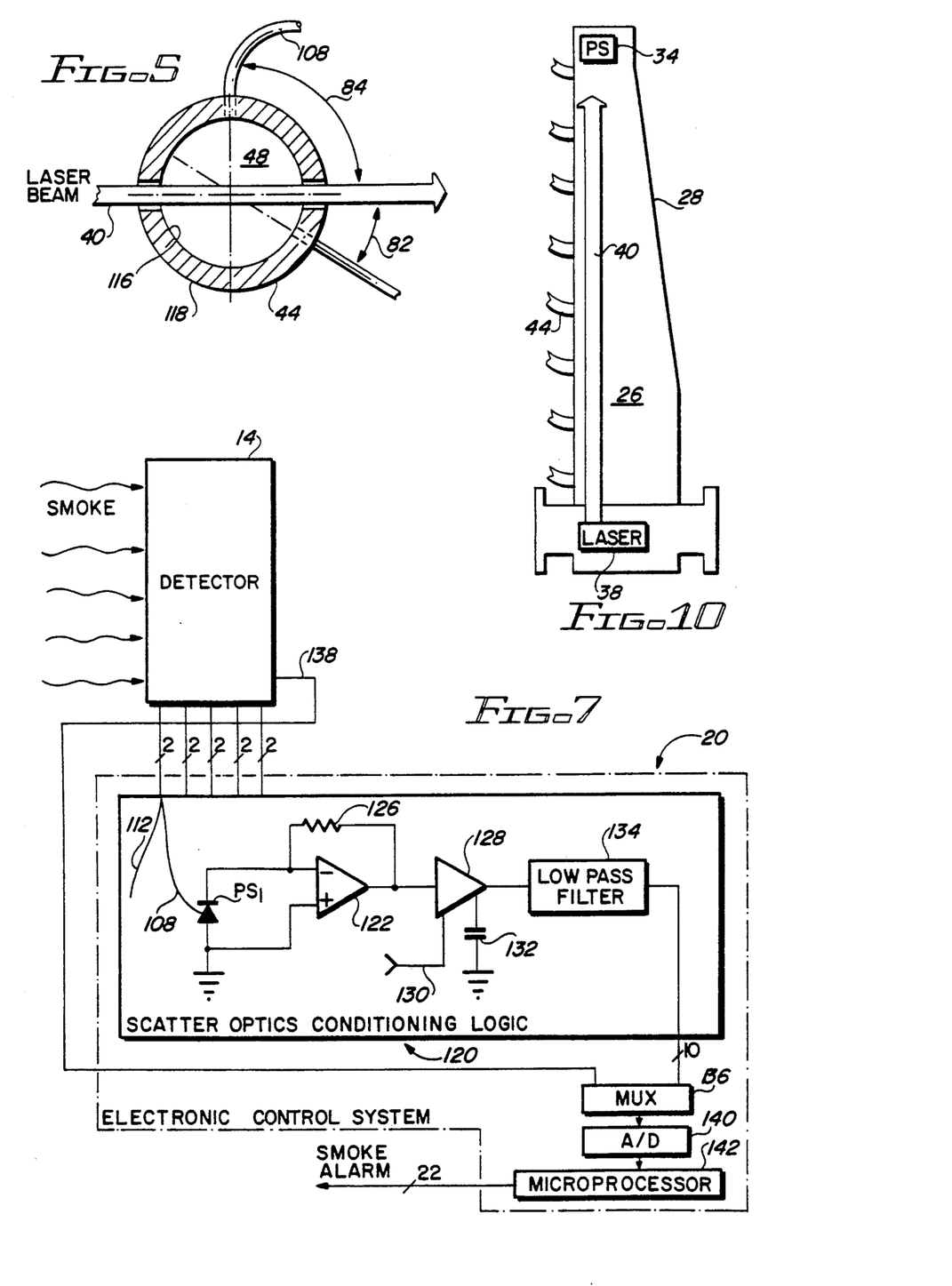
FIG. 5 is a partially cross-sectional and partially elevational view taken as indicated in FIG. 6.
FIG. 7 is a schematic diagram of the electronic control system indicated in FIG. 1.
FIG. 10 is a highly schematic illustration of the embodiment of FIG. 4.
Figure 6:
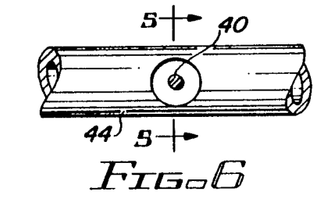
FIG. 6 is a fragmentary elevational view of a tubular conduit taken as indicated in FIG. 2.

Each of the conduits 44 has two aligned holes formed between its interior and exterior surfaces 116, 118 to provide a path for the beam 40, as is indicated in FIG. 5, and all are collectively positioned such that their holes are in optical alignment. The lasers 38, 76 are positioned so that in operation each directs its beam through said holes and to the reference photodiode 86 (FIG. 11) of the opposing laser. Each of the conduits 44 is provided with two additional holes extending between its interior and exterior surfaces 116, 118 to provide for fitting the fiber optics 108, 112, as is indicated in FIG. 5. The first set of fiber optics 108 are fitted such that their ends project into the channel 48 to a point at which they are about 0.254 centimeters from the beam 40. The second set of fiber optics 112 are fitted such that their ends are substantially flush with the interior surface 116.

The laser or lasers 38, 76 are preferably selected to produce a beam of visible light for reasons of both safety and performance. In general, superior performance is observed for shorter wavelengths. In testing, favorable results were obtained with a laser which emitted a beam of visible light at 785 nanometers wavelength. Results were considerably improved by replacing the laser with one which emitted a beam at 675 nanometers wavelength.

Figure 8:
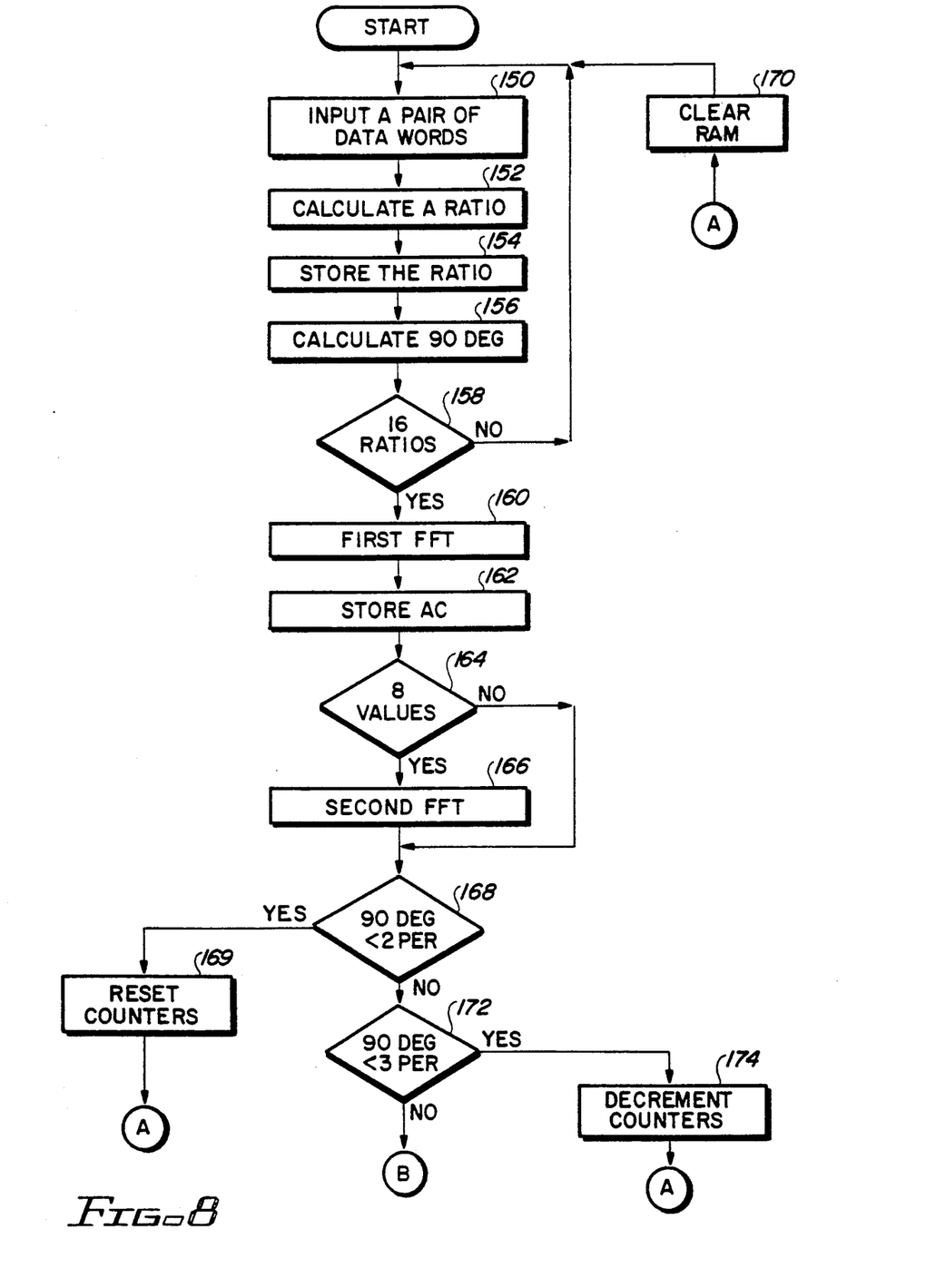
FIGS. 8 and 9 are flowcharts of a microprocessor program for detecting smoke in use of the embodiment illustrated in FIGS. 2, 3, 5, and 6.
Figure 9:
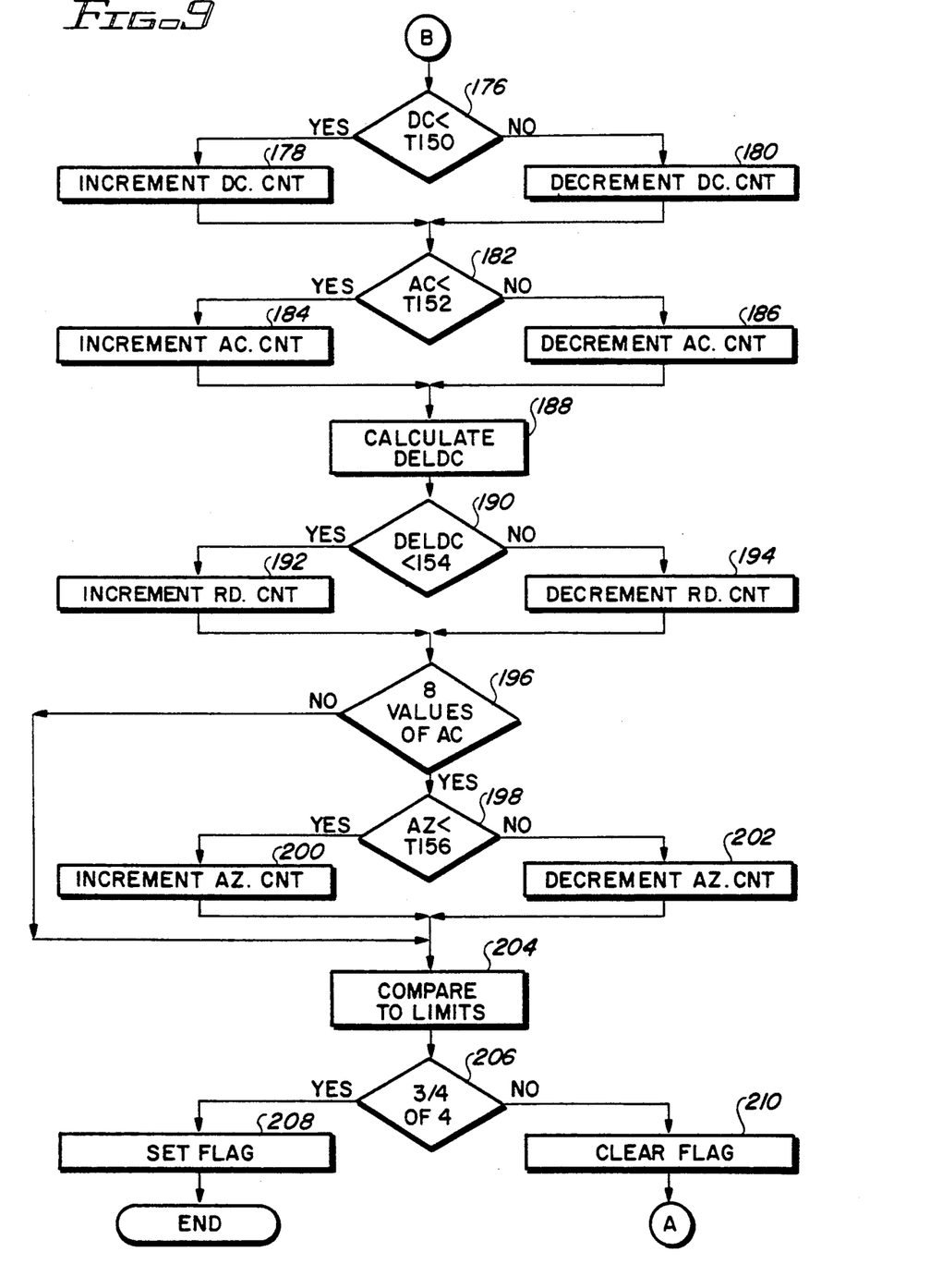

The preferred embodiments of the smoke detector 14 having been described, attention is now directed to FIGS. 7-9 which illustrate the essential hardware of the ECS 20, as well as a preferred control algorithm for detecting and indicating status and/or an alarm condition.

Referring now to FIG. 7, there is shown the electronics control system 20 for the smoke detection system. Five pairs of fiber optics elements 108 and 112 supply light signals from their corresponding tubes to the scatter optics conditioning logic 120. In each pair of fiber optics elements 108 and 112, the first fiber optics element 108 supplies a signal whose intensity indicates the amount of scattering at ninety degrees, and the second fiber optics element 112 supplies a signal whose intensity indicates the amount of scattering at thirty degrees. For each one of the ten fiber optics elements, the scatter optics conditioning logic 120 converts a light signal to an electrical signal. A photosensor $PS_1$, whose anode is coupled to a reference potential, is placed flush against the end of the fiber optics element 108. The photosensor $PS_1$ can be, for example, a photodiode. An output signal from the photosensor $PS_1$ is amplified by a first operational amplifier 122 and first resistor 126. As a matter of design, different gains are selected from the signals indicating scattering at thirty and ninety degrees, respectively. Considerations for this selection include, but are not limited to, the amount of scattered light detected at 30 degrees and 90 degrees. The output of the first operational amplifier 122 is supplied to an input of second operational amplifier 128 and capacitor 132, which functions to sample and hold the signal. A sample command is supplied to the second operational amplifier 128 on a first conductor 130. The output of the second operational amplifier 128 is supplied to a low pass filter 134. The type of low pass filter 134 and its cutoff frequency are chosen as a matter of design. For example, the low pass filter 134 can be a third order butterworth filter having a cutoff frequency of 30 Hz.

A signal from a reference photodiode 86 on the auxiliary laser 76, which forms a part of the smoke detector 14, is supplied to an analog multiplexer 136 via a second conductor 138. The function of the signal on the second conductor 138 is to detect mechanical shifts in the main laser 38 that the internal reference photodiode of the main laser would not otherwise detect. The output of each low pass filter 134 is supplied in parallel to the multiplexer 136. In all, there are ten inputs from the low pass filters 134. The multiplexer 136 is controlled to provide a serial stream of analog signals. The period of each signal in the stream is 50 microseconds. The analog output of the multiplexer 136 is supplied to an analog to digital (A/D) converter 140. The A/D converter provides a serial stream of digital data words which correspond to the analog signals. The output of the A/D converter is supplied to a microprocessor 142. Data words are supplied to the microprocessor 142 at a rate of 250 Hz, i.e., once every 4 milliseconds.

The microprocessor 142 processes each pair of word supplied by the multiplexer 136 to detect smoke in the corresponding tube. The microprocessor 142 can be any commercially available type, such as the Intel 80C196. The architecture of this microprocessor is well known; therefore, a detailed description is not necessary. The microprocessor program is stored in external memory, such as ultraviolet programmable read-only memory 144. All variables utilized by the microprocessor 142 are stored in random access memory 146. The output of the microprocessor 142, which may indicate status or a smoke alarm condition for each tube, is sent over a data bus 22 to a controller which communicates with a display panel and/or smoke alarm.

Referring now to FIGS. 8 and 9, there is shown a flow chart of the microprocessor program that processes the pairs of digital data words. Processing is described only for one channel, but is the same for each channel. Every four milliseconds, a pair of data words is input to the microprocessor (module 150). The first and second digital words of the pair correspond to the intensity of light scattered towards the fiber optics elements at thirty degrees and ninety degrees, respectively. At ninety degrees, the amount of scattering is substantially independent of particle size; therefore, the second data word indicates the presence of all particulate matter, including smoke and dust, within the tube. At thirty degrees, in contrast, the amount of scattering is significantly dependent on the size of the particle. Scattering is greater for larger particles such as dust than for the relatively smaller particles found in smoke. Thus, the first data word, which corresponds to scattering at thirty degrees, can be used in conjunction with the second data word to distinguish between dust and smoke.

The microprocessor calculates a scattering ratio by dividing the second data word into the first data word (module 152). The ratio indicates the amount of smoke per amount of total obscuration, i.e., the percentage of smoke in the tube. Since the scattering at thirty degrees for dust is greater than it is for smoke, the ratio for a given percentage of pure dust is greater than the ratio for the same percentage of pure smoke. The ratio is stored in random access memory RAM (module 154).

A weighted average 90DEG of the second digital word is also calculated by the microprocessor (module 156). Until sixteen ratios for a given tube are stored in random access memory RAM (module 158), the microprocessor continues to input pairs of data words for the given tube (module 150). Once sixteen ratios are stored, the microprocessor performs a first fast fourier transform on the sixteen ratios (module 160). The first fast fourier transform analyzes the frequency spectrum of the ratios and yields a steady state component DC and a component AC which corresponds to the fundamental frequency. The steady state component DC indicates the average value of the sixteen ratios over a 64 millisecond period. The amplitude of the frequency component AC indicates the amount of variation among the sixteen samples over the sixty four millisecond period. Thus, the frequency of resolution is roughly thirty hertz, i.e., the fast fourier transform can detect changes in the sixteen ratios that exceed thirty hertz.

After deriving the steady state and frequency components DC and AC of the sixteen ratios, the microprocessor stores the fundamental frequency component AC in random access memory (module 162). Once eight values of the fundamental frequency component are stored in random access memory RAM (module 164), the microprocessor performs a second fast fourier transform (module 166). Here, the second fast fourier transform is performed on one hundred and twenty eight points, which increases the frequency from roughly thirty hertz to roughly four hertz. Only the fundamental frequency component AZ is processed. The fundamental frequency is largely a function of the rate at which the particles flow through the tube. For instance, with a high flow rate, many more particles are detected over sixty four milliseconds; therefore, more changes in the ratio b occur. In contrast, with a low flow rate, fewer particles are detected over the sixty four milliseconds; therefore, fewer changes in the ratio occur. In a sixteen point fast fourier transform, there are not enough ratios to detect a low frequency change. However, in a 128 point fast fourier transform, there are enough ratios to detect low frequency changes. Therefore, with the second fast fourier transform, changes in the ratios can be detected for low flow rates. It should be noted that the second fast fourier transform (module 166) can only supplement the first fast fourier transform (module 160). It cannot stand alone. To accumulate ratios for the second fast fourier transform, over half a second would be required. This is too long a period of time to detect smoke. However, in conjunction with the sixty four millisecond period of the first fast fourier transform (module 160), smoke can be detected in accordance with commercial expectations and at low flow rates.

After performing the first fast fourier transform (module 160), the microprocessor performs a series of comparisons to determine whether there is smoke in the tube. The steady state and fundamental frequency components DC and AC are compared to six parameters: a first parameter 2PER, whose value is the amount of scattering at ninety degrees when the intensity of the laser beam is reduced by two percent per foot; a second parameter 3PER, whose value is the amount of scattering at ninety degrees when the intensity of the laser beam is reduced by three percent per foot; a third parameter T150, whose value is the steady state component DC at which smoke occurs in the tube; a fourth parameter T152, whose value is the fundamental frequency component AC at which smoke occurs in the tube; a fifth parameter T154, whose value is the rate of change in steady state components at which smoke occurs over successive samples; and a sixth parameter T156, whose value is the fundamental frequency component AZ, derived from a 128 point fast fourier transform, at which smoke occurs in the tube. These parameters are derived experimentally. In a test atmosphere, dust is injected until the intensity of a laser beam is reduced by one percent. A fast fourier transform of sixteen ratios is taken, and the values for the resulting steady state and fundamental frequency components are calculated. Additionally, a fast fourier transform of 128 ratios is taken, and the fundamental frequency component is calculated. Also, the weighted average of scattering at ninety degrees is calculated for sixteen samples. This procedure is repeated for atmospheres into which dust is injected until the intensity of the laser beam is reduced by two 2 percent per foot and three percent per foot, respectively. The procedure is then repeated three more times, except that smoke is injected into the test atmosphere instead of dust. From the measurements taken from these six test atmospheres, the six parameters 2PER, 3PER, T150, T152, T154 and T156 are derived. The first and second parameters 2PER and 3PER can be the weighted average for either smoke or dust. The third parameter T150 is the average of the steady state components for dust and smoke at three percent reduction per foot in intensity of the laser beam. The fourth parameter T152 is the average of the fundamental frequency components for dust and smoke at three percent reduction per foot in intensity of the laser beam. The sixth parameter T156 is the average of the fundamental frequency components derived from the 128 point fast fourier transform for dust and smoke at three percent reduction in intensity of the laser beam. The fifth parameter T154 is derived from plots of the ratio versus time. As dust is injected into the test atmosphere from two percent to three percent obscuration, the ratios are plotted versus time. For this plot, a line is fitted by such means as a least squares regression. A similar graph is plotted for smoke. The average of the slopes for dust and smoke reflects the rate change in the steady state due to smoke. It should be noted that the third, fourth, fifth and sixth parameters T150, T152, T154 and T156 do not have to be the average of components for dust and smoke. However, each parameter should be selected to reflect the presence of smoke in the tube. The six parameters are stored in random access memory RAM for use by the microprocessor.

By using the first and second parameters 2PER and 3PER, the microprocessor determines whether there is sufficient particulate matter in the tube to warrant an alarm. If the amount of scattering in the tube at ninety degrees is less than 2PER (module 168), then there is no alarm condition. The microprocessor resets first, second, third and fourth counters, DCCNT, ACCNT, RDCNT and AZCNT (module 169), clears RAM (module 170) and then inputs a pair of data words for a new block of ratios (module 150). These counters indicate whether smoke has been detected according to the steady state component, fundamental frequency component AC level, AC level, rate of change steady state level over successive sampling periods, and fundamental frequency AZ, respectively. If, however, the amount of scattering at ninety degrees is greater than 2PER but less than 3PER (module 172), the microprocessor decrements the four counters DCCNT, ACCNT, RDCNT and AZCNT (module 174), clears RAM (module 170) and inputs a pair of data words for a new block of ratios (module 150). This is to correct the counters for fluctuations caused by bounce and hysteresis during successive samples. If the amount of scattering at ninety degrees is greater than 3PER (module 174), the microprocessor determines whether the particulate matter includes smoke. If the steady state component DC is less than the first parameter T150 (module 176), the microprocessor increments the first counter DCCNT (module 178). Otherwise, the first counter DCCNT is decremented (module 180). If the fundamental frequency component AC is less than the second parameter T152 (module 182), the microprocessor increments the second counter ACCNT (module 184). Otherwise, the second counter ACCNT is decremented (module 186). Next, the microprocessor calculates the rate of change DELDC, which is the difference in successive samples of the steady state component DC over a sampling period, which is 64 milliseconds (module 188). If the rate of change DELDC of the steady state components over successive samples is less than the third parameter T154 (module 190), the microprocessor increments the third counter RDCNT (module 192). Otherwise, the third counter RDCNT is decremented (module 194). If eight values of the fundamental frequency AC are stored in RAM (module 196), the microprocessor examines the fundamental frequency AZ. If the fundamental frequency component AZ is less than the fourth parameter T156 (module 198), the fourth counter AZCNT is incremented (module 200). Otherwise, the microprocessor decrements fourth counter AZCNT (module 202). The four counters DCCNT, ACNT, RDCNT and AZCNT are continuously updated.

The first, second, third and fourth counters DCCNT, ACCNT, RDCNT and AZCNT are compared to first, second, third and fourth limits DCLIM, ACLIM, RDLIM and AZLIM, respectively (module 204). If at least three of the four limits DCLIM, ACLIM, RDLIM and AZLIM are exceeded (module 206), a flag indicating the presence of smoke is set (module 208). Thus, during one sample period of sixty four milliseconds, if three of the four counters indicate smoke, the smoke alarm will be triggered. If less than three of the four limits DCLIM, ACLIM, RDLIM and AZLIM are exceeded (module 206), the flag is set to the value zero (module 210), the microprocessor clears RAM (module 170) and inputs a pair of data words for a new block of ratios (module 150). The four limits DCLIM, ACLIM, RDLIM and AZLIM are determined by experimentaion and experience.

What is claimed is:

1. Detection apparatus, comprising:
   a first manifold forming a plenum;
   means connected to said first manifold for forming a plurality of spatially separate channels in fluid communication with said plenum, each said channel supplying a corresponding sample flow to said plenum;
   laser means for directing a beam of electromagnetic radiation relative to the channels such that said sample flows can intersect said beam in flowing along the channels to the plenum; and
   detecting means, operatively associated with the channels, for detecting electromagnetic radiation scattered by said sample flows.

2. The invention of claim 1 further comprising exhaust means for removing said sample flows from said plenum, said exhaust means including a second manifold attached to said first manifold and in fluid communication with said plenum.

3. The invention of claim 2, further comprising blower means, coupled to said second manifold, so as to be operable to effect sample flow from said channels to said plenum.

4. The invention of claim 1 wherein said forming means comprises a plurality of conduits having longitudinal axes, each conduit having both an interior surface defining its associated channel and an exterior surface transversely surrounding the interior surface, each conduit being provided with two holes extending from its exterior surface to its interior surface, the conduits being collectively positioned such that all of said holes are in optical alignment, said laser being positioned to direct its beam through said holes.

5. The invention of claim 4 wherein said detecting means includes a plurality of photosensors, at least one being operatively associated with each channel such that radiation scattered can impinge the photosensor.

6. The invention of claim 5 wherein each conduit is provided with at least one additional hole extending from its exterior surface to its interior surface, the additional holes being located to receive radiation scattered, wherein said detecting means further comprises a plurality of fiber optics, each fiber optics transmitting scattered light to an associated one of said photosensors.

7. The invention of claim 1 further comprising a photosensor secured to said first manifold and positioned relative to said laser means to receive said beam.

8. The invention of claim 4 wherein said laser means includes a first laser for directing said beam through said holes and into said plurality of sample flows; a second laser for directing a second beam of electromagnetic radiation in a direction substantially opposite said beam from said first laser, and means for actuating either said first laser or said second laser.

9. The invention of claim 8 further comprising a first photosensor positioned opposite said first laser to receive said first laser beam that has passed through said sample flows; and a second photosensor positioned opposite said second laser to receive said second laser beam that has passed through said sample flows.

10. The invention of claim 9 wherein said first laser and second photosensor comprise a first photodiode, and wherein said second laser and first photosensor comprise a second photodiode.

11. Apparatus for detecting particulate matter in a plurality of sample flows, comprising:
   a first laser for directing a first beam of electromagnetic radiation into said plurality of sample flows;
   a second laser positioned to direct a second beam of electromagnetic radiation in a direction substantially opposite that of the first beam such that the first and second beams are substantially aligned;
   detector means for detecting the electromagnetic radiation scattered by each sample flow; and
   means for acutating either said first laser of said second laser.

12. The invention of claim 11 further comprising a first photosensor positioned opposite said first laser to detect radiation transmitted from said first laser that has passed through the sample flows; and a second photosensor positioned opposite said second laser to detect radiation transmitted from the second laser that has passed through the sample flows.

13. The invention of claim 12 wherein said first laser and second photosensor comprise a first photodiode, and wherein said second laser and first photosensor comprise a second photodiode.

14. Apparatus for detecting particles in a number n of sample flows, where $n \geq 1$, comprising:
   illuminating means for directing a beam of electromagnetic radiation into said n sample flows; and
   first and second detector means for detecting said electromagnetic radiation scattered by each said sample flow, said first detector means detecting said radiation scattered at a first angle from said beam, said second detector means detecting said radiation scattered at a second angle from said beam.

15. Apparatus according to claim 14, wherein said first angle is between 85 and 95 degrees from said beam.

16. Apparatus according to claim 14, wherein said second angle is between 5 and 35 degrees from said beam.

17. Apparatus according to claim 14, wherein said first angle is approximately 90 degrees from said beam and wherein said second angle is approximately 30 degrees from said beam.

18. Apparatus according to claim 14, wherein said number n of sample flows is greater than one, wherein said sample flows are arranged in seriatim, and wherein said illuminating means includes a first laser for directing a laser beam into each of said sample flows.

19. Apparatus according to claim 18, wherein said illuminating means further includes
- a second laser for directing a laser beam into each of said sample flow, said first and second lasers being positioned such that said lasers direct their beams in opposite directions; and
- means for actuating either aid first laser or said second laser.

20. Apparatus according to claim 19, wherein said illuminating means further includes a first photodiode positioned opposite said first laser to detect radiation transmitted from said first laser that has passed through the sample flows; and a second photodiode positioned opposite said second laser to detect radiation transmitted from the second laser that has passed through the sample flows.

* * * * *